United States Patent [19]

Baldwin et al.

[11] Patent Number: 4,996,321

[45] Date of Patent: Feb. 26, 1991

[54] DIBENZO[A,D]CYCLOHEPTENYLIDENE COMPOUNDS

[75] Inventors: John J. Baldwin, Gwynedd Valley; David C. Remy, North Wales, both of Pa.

[73] Assignee: Merck & Co., Inc., Rahway, N.J.

[21] Appl. No.: 484,963

[22] Filed: Feb. 26, 1990

[51] Int. Cl.$^5$ .............................................. C07D 211/70
[52] U.S. Cl. .................................... 546/194; 546/203
[58] Field of Search ................................ 546/194, 203

[56] References Cited

U.S. PATENT DOCUMENTS

| | | | |
|---|---|---|---|
| 3,326,924 | 6/1967 | Villani | 546/194 |
| 4,020,169 | 4/1977 | Remy et al. | 549/27 |
| 4,031,222 | 6/1977 | Remy | 514/325 |

OTHER PUBLICATIONS

Ganapathi et al., *Cancer Research*, 43, 3696 (1983).
Randall et al., *J. Med. Chem.*, 22, 1222 (1979).
Remy et al., *J. Org. Chem.*, 41, 1644 (1976).
Remy et al., *J. Med. Chem.*, 20, 1013 (1977).
Rogan et al., *Science*, 224, 994 (1984).
Rothenberg et al., *J. Nat. Cancer Inst.*, 81, 907 (1989).
Tsuruo et al., *Cancer Research*, 41, 1967 (1981).
Tsuruo et al., *Cancer Research*, 42, 4730 (1982).
Tsuruo et al., *Cancer Research*, 43, 2905 (1983).

*Primary Examiner*—Mary C. Lee
*Assistant Examiner*—Jacqueline Haley
*Attorney, Agent, or Firm*—Hesna J. Pfeiffer; Raymond M. Speer; William H. Nicholson

[57] ABSTRACT

Various cyproheptadine derivatives sensitize multidrug resistant cells to certain chemotherapeutic agents. As such, these cyproheptadine derivatives are useful as adjuncts in the reversal of multidrug resistance in mammalian tumor cells either as compounds, pharmaceutically acceptable salts, or pharmaceutical composition ingredients in combination with anticancer chemotherapeutic agents or compounds.

1 Claim, No Drawings

DIBENZO[A,D]CYCLOHEPTENYLIDENE COMPOUNDS

The present invention is concerned with the compounds (−)-1-cyclopropylmethyl-4-(3-trifluoromethylthio-5H-dibenzo[a,d]cyclohepten-5-ylidene)piperidine, (+)-1-cyclopropylmethyl-4-(3-iodo-5H-dibenzo[a,d]cyclohepten-5-ylidene)piperidine, 4-amino-5-chloro-2-methoxy-N-((5-(1-methyl-4-piperidinyylidene)-5H-dibenzo[a,d]cyclohepten-3-yl)methyl)benzamide, 3,4,5-trimethoxy-N-((5-(1-methyl-4-piperdinylidene)-5H-dibenzo[a,d]cyclohepten-3-yl)-methyl)benzamide and diethyl 1,4-dihydro-2,6-dimethyl-4-(5-(1-methyl-4-piperidinylidene)-5H-dibenzo[a,d]cyclohepten-3-yl)pyridinedicarboxylate or pharmaceutically acceptable salts thereof which are useful as adjuncts in treating cancer and, more specifically, it relates to a method reversing multidrug resistance in patients afflicted with multidrug resistant tumors.

BACKGROUND OF THE INVENTION

A major problem in the treatment of cancer is the emergence of tumor cell resistance to chemotherapeutic agents and the subsequent patient relapse. These cancer victims may fail to respond to any antitumor agent since these tumor cells tend to exhibit clinical resistance to many drugs. This phenomenon is termed multidrug resistance (MDR). MDR is associated with certain alterations in tumor cells, including an over-expression of a certain high molecular weight membrane glycoprotein and a decrease in the ability of the tumor cell to accumulate and retain chemotherapeutic agents.

Drugs of proven antitumor chemotherapeutic value to which multidrug-resistance has been observed include vinblastine, vincristine, etoposide, teniposide, doxorubicin (adriamycin), daunorubicin, plicamycin (mithramycin) and actinomycin D. Many tumors are intrinsically multidrug-resistance (e.g. adenocarcinomas of the colon and kidney) which other tumors acquire multidrug-resistance during therapy (e.g. neuroblastomas and childhood leukemias).

Agents are available which can restore drug sensitivity to some multidrug resistant tumor cells. Among these agents known to possess this property are calcium transport blockers (e.g. verapamil) and calmodulin inhibitors (e.g. trifluoperazine). Clinical use of these compounds has been limited by their extremely toxic side effects (Twentyman, P. R. et al., *Int. J. Radiat. Oncol. Biol. Phys.*, 12, 1355 (1986).

The present invention describes a use for various cyproheptadine derivatives that are effective in increasing the sensitivity of tumor cells resistant to anticancer chemotherapeutic agents, such as vinblastine. These compounds have the effect, as described herein, of reducing the resistance of multidrug resistant tumor cells and potentiating the sensitivity of cells susceptible to antitumor agents.

Given their efficiency in reversing multidrug resistance, these compounds are expected to have broad clinical application and may play a significant role in fighting cancer.

An object of the present invention is to provide a method for increasing the sensitivity of tumor cells which are susceptible to certain antitumor agents using (−)-1-cyclopropylmethyl-4-(3-trifluoro-methylthio-5H-dibenzo[a,d]cyclohepten-5-ylidene)-piperidine, (+)-1-cyclopropylmethyl-4-(3-iodo-5H-dibenzo[a,d]cyclohepten-5-ylidene)piperidine, 4-amino-5-chloro-2-methoxy-N-((5-(1-methyl-4-piperidinylidene)-5H-dibenzo[a,d]cyclohepten-3-yl)methyl)benzamide, 3,4,5-trimethoxy-N-((5-(1-methyl-4-piperdinylidene)-5H-dibenzo[a,d]cyclohepten-3-yl)-methyl)benzamide and diethyl 1,4-dihydro-2,6-dimethyl-4-(5-(1-methyl-4-piperidinylidene)-5H-dibenzo[a,d]cyclohepten-3-yl)-pyridinedicarboxylate or a pharmaceutically acceptable salt thereof.

An additional object of the present invention is to provide a method for treating multidrug resistant or drug sensitive tumor cells which preferably involves administering to a patient in need of such treatment a therapeutically effective dosage of a compound of this invention in combination with, prior to or concurrent to the administration of a therapeutically effective dosage of an antitumor chemotherapeutic agent.

A further object of this invention relates to a method of preventing the emergency of multidrug resistant tumor cells during a course of treatment with antitumor chemotherapeutic agents.

A still further object of this invention is to provide a method reducing the effective dosage of an antitumor chemotherapeutic agent during a course of treatment.

The present invention has met the above described need by providing a method which preferably involves administering to a person a therapeutically effective dosage of a compound of this invention in combination with or concurrent to the administration of a therapeutically effective dosage of an antitumor chemotherapeutic agent for the direct treatment of multidrug resistant tumors. In addition, the compounds of the present invention may have a lower propensity to induce extrapyramidal side effects that are experienced with many tricyclic compounds.

SUMMARY OF THE INVENTION

This invention is concerned with the use of the compounds (−)-1-cyclopropylmethyl-4-(3-trifluoromethylthio-5H-dibenzo[a,d]cyclohepten-5ylidene)piperidine, (+)-1-cyclopropylmethyl-4-(3-iodo-5H-dibenzo[a,]cyclohepten-5ylidene)piperidine, 4-amino-5-chloro-2-methoxy-N-((5-(1-methyl-4-piperdinylidene)-5H-dibenzo[a,d]cyclohepten-3-methyl)benzamide, 3,4,5-trimethoxy-N-((5-(1-methyl-4-piperidinylidene)-5H-dibenzo[a,d]cyclohepten-3yl)methyl)benzamide or diethyl 1,4-dihydro-2,6-dimethyl-4-(5-(1-methyl-4-piperidinylidene)-5H-dibenzo[a,d]cyclohepten-3-yl)pyridinedicarboxylate or a pharmaceutically acceptable non-toxic salt thereof, with anticancer agents in the treatment of multidrug resistant tumors and the treatment of cancer.

It has been discovered that the compounds of the present invention have the ability to sensitive multidrug resistant tumor cells to antitumor chemotherapeutic agents, such as vinblastine. It has also been discovered that these compounds have the ability to potentiate the sensitivity of tumor cells susceptible to these antitumor chemotherapeutic agents. Due to these properties, the compounds of the present invention are expected to have broad clinical application and major significance.

This invention relates to a method of sensitizing multidrug resistant tumor cells to antitumor chemotherapeutic agents. It also relates to a method of preventing the emergence of multidrug resistant tumor cells during a course of treatment with antitumor chemotherapeutic agents. In addition, this invention relate to a method of reducing the effective dosage of an antitumor chemotherapeutic agent during the course of treatment of multidrug resistant tumors. It has been found that the compounds of the present invention have the activity of increasing the sensitivity of multidrug resistant mammalian cells in culture.

The compounds of the present invention possess activity in reversing multidrug resistance and are useful as adjuncts in the treatment of multidrug resistant tumors.

For these purposes, the compounds of the present invention may be administered orally, parenterally (including subcutaneous injections, intravenous, intramuscular, intrasternal injection or infusion techniques) or rectally, in dosage unit formulations containing conventional non-toxic, pharmaceutically-acceptable carriers, adjuvants and vehicles.

This invention also relates to a method of treatment of patients afflicted with multidrug resistant tumors involving the administration to a patient in need of such therapy a pharmaceutical composition comprising a pharmaceutical carrier and a therapeutically-effective amount of a compound of the present invention or a pharmaceutically acceptable acid addition salt thereof, in combination with an antitumor chemotherapeutic agent. This invention further relates to a method for the reversal of multidrug resistance in patients in patients afflicted with multidrug resistant tumors involving the administration to a patient in need of such therapy a pharmaceutical composition comprising a pharmaceutical carrier and a therapeutically-effective amount of a compound of the present invention or a pharmaceutically acceptable acid addition salt thereof, alone or in combination with cancer chemotherapeutic agents.

As implied earlier, the compounds of the present invention may be administered by a variety of established methods, including intravenously, intramuscularly, subcutaneously, extracorporeally, and orally. Since the compounds of the present invention exhibit appreciable oral activity, the preferred mode of administration is that in which a compound of this invention is administered orally. However, parenteral administration may be preferable in certain circumstances and the precise mode of administration is left to the discretion of the practitioner.

DETAILED DESCRIPTION OF THE INVENTION

The compounds useful as the active ingredient in the composition of the present invention are:

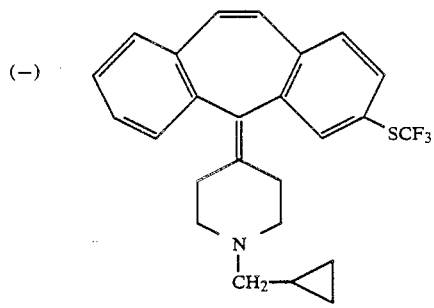

(−)-1-cyclopropylmethyl-4-(3-trifluoromethyl-thio-5H-dibenzo[a,d]cyclohepten-5-ylidene)piperidine;

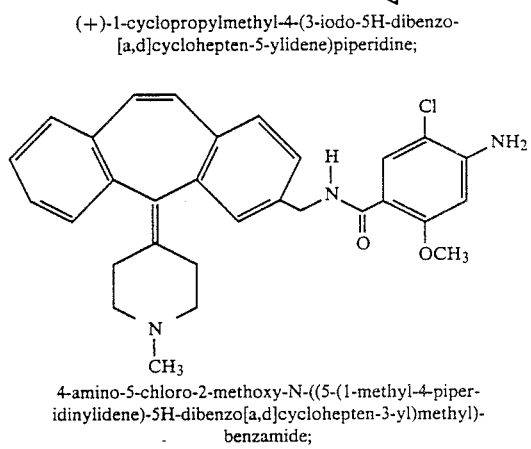

(+)-1-cyclopropylmethyl-4-(3-iodo-5H-dibenzo-[a,d]cyclohepten-5-ylidene)piperidine;

4-amino-5-chloro-2-methoxy-N-((5-(1-methyl-4-piperidinylidene)-5H-dibenzo[a,d]cyclohepten-3-yl)methyl)-benzamide;

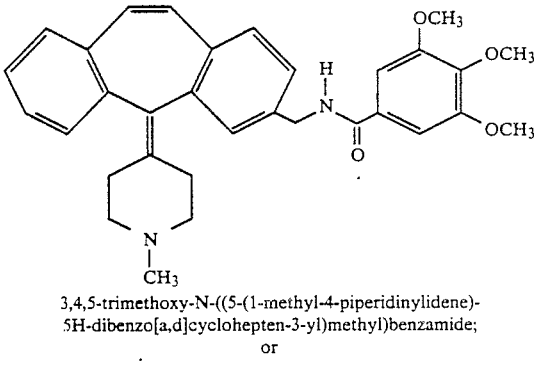

3,4,5-trimethoxy-N-((5-(1-methyl-4-piperidinylidene)-5H-dibenzo[a,d]cyclohepten-3-yl)methyl)benzamide;
or

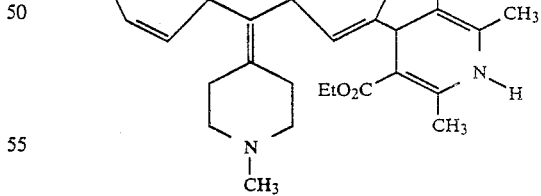

diethyl 1,4-dihydro-2,6-dimethyl-4-(5-(1-methyl-4-piperidinylidene)-5H-dibenzo[a,d]cyclohepten-3-yl)-pyridinedicarboxylate, or pharmaceutically acceptable salts thereof.

The compounds (−)-1-cyclopropylmethyl-4-(3-trifluoromethylthio-5H-dibenzo[a,d]cyclohepten-5-ylidene)piperidine and (+)-1-cyclopropylmethyl-4-(3-iodo-5H-dibenzo[a,d]cyclohepten-5-ylidene)piperidine are described as substances as useful in treating psychoses in U.S. Pat. No. 4,031,222, issued June 21, 1977, of David C. Remy, which is incorporated herein by reference.

The preparation and use of 4-amino-5-chloro-2-methoxy-N-((5-(1-methyl-4-piperidinylidene)-5H-dibenzo[a,d]cyclohepten-3-yl)methyl)benzamide, 3,4,5-trimethoxy-N-((5-(1-methyl-4-piperidinylidene)-5-dibenzo[a,d]cyclohepten-3-yl)methyl)benzamide and diethyl 1,4-dihydro-2,6-dimethyl-4-(5-(1-methyl-4-piperidinylidene)-5H-dibenzo[a,d]cyclohepten-3-yl-pyridinedicarboxylate are described herein.

The compounds of the present invention are capable of enhancing the sensitivity of multidrug resistant tumor cells to antitumor chemotherapeutic agents. In addition, the compounds of the present invention are useful in preventing the emergence of multidrug resistant tumor cells during a course of treatment with antitumor chemotherapeutic agents. The compounds of the present invention are futher useful in reducing the effective dosage of an antitumor chemotherapeutic agent during a course of treatment of multidrug resistant tumors.

Important antitumor chemotherapeutic agents (with the usual effective dosage) to which clinical multidrug resistance has been observed include vinblastine (0.1 mg per kilogram per week), vincristine (0.1 mg per kilogram per week), dactinomycin (0.015 mg per kilogram per day), daunorubicin (60 to 75 mg per square meter per week), doxorubicin (500 to 600 mg per square meter), etoposide (35 to 50 mg per square meter per day), and mithramycin (0.025 mg per kilogram per day). Multidrug resistance has been shown to occur in vitro as well as in the clinic.

Multidrug resistant cells lines are easily obtainable for in vitro determination of drug sensitization by compounds of the present invention, as well as other compounds with similar activity. These cell lines include NIH-OVCAR-3 (ATCC HTB161)., which is commercially available. Other cell lines can be readily developed in accordance with the methods described by Twentyman et al., Br. J. Cancer, 54, 253 (1986). This procedure selects for multidrug resistant cells by culturing the parental drug sensitive cell line in the continued presence of a cytotoxic drug, for example, doxorubicin. Drug sensitive cells will perish while multidrug resistant cells will survive and grow despite the presence of the drug. Eventually, a multidrug resistant cell population emerges and can be used in an assay system for the detection of agents which can modify the multidrug resistance. Many cell lines are suitable as parental cell lines from which multidrug resistant cells can be selected. These cell lines can be derived from humans or other mammals and can be derived from normal tissue or tumor tissue. Commercially available human cell lines derived from human tumor tissue include KB (ATCC CCL 17), NCI-H69 (ATCC HTB 119), CCRF-CCM (ATTC CCL 119), and K-562 (ATCC CCL 243). Other suitable, commercially available mammalian cells lines include LM(TK-) (ATCC CLL 1.3), and CHO-K1 (ATCC CCL 61).

The sensitivity of drug resistant cell lines can be compared with the parenteral cell line by assaying inhibition of cell growth during continuous exposure to the drug. Growth of the parental cells will be inhibited while the growth of resistant cells will not be inhibited. Cell growth can be measured by cell counting using an electronic cell counter, for example, a Coulter Counter, Coulter Electronics, Herts, England, and following the manufacturers recommended instructions for use. Cells may also be counted microscopically using a hemocytometer, but the electronic cell counter is preferred.

Cell growth can be measured by other techniques including cell staining. Cells can be stained by various agents including crystal violet, coomassie blue and methylene blue with methlene blue the preferred stain. Determining cell growth by methylene blue staining can be done as follows.

Equal numbers of cells of an anchorage dependent mammalian cell line are seeded in growth medium (e.g. alpha MEM plus 10% FBS) into a suitable culture vessel, e.g. plastic 96 well tissue culture plates. A cytotoxic drug (e.g. doxorubicin) is added to the cells in the dishes at various concentrations ranging between 0 and 100 $\mu$m. Following about 72 hours of continuous exposure to the cytotoxic agent, the growth medium is decanted and the cells are washed with a suitable buffer, e.g. phosphate buffered saline (PBS). About 2 ml of a solution of 2% methylene blue (dissolve methylene blue in a solution of about 50% ethanol in water) is added to the cells on the dishes. The dye is allowed to contact the cells for about 2 minutes. Excess dye is washer away with cold water and the plates are air dried. The dye stained cells are then solubilized by adding an equal volume to all wells of a solution of a detergent, e.g. 1% N-lauroyl-sacrosine. The amount of dye remaining in the wells directly correlates with the number of cells in the well. The amount of methylene blue dye in the wells can be measured spectrophotometrically by measuring absorbance at 600 nm using an electronic ELISA plate spectrophotmeter (Minireader II, Dynatech Laboratories, Alexandria, Va.). The typical results show decreased absorbance at 600 nm with increasing cytotoxic drug concentration indicating increased cell death with increased drug concentration.

Cell growth measured by either the cell counting method or the cell staining method should closely correlate. The staining method is preferable because of its simplicity and it is easily adaptable to automation which allows many experiments to be performed with many test compounds non-labor intensively.

Radiolabelled compounds may also be utilized to determine the accumulation of antitumor chemotherapeutic agents in drug sensitive cells and in multidrug resistant cells. For example, the accumulation of [$^3$H]vinblastine by drug sensitive cell lines and drug resistant cells lines in the presence or absence of a test compound may be determined. The relative accumulation of the radiolabelled chemotherapeutic agent is indicative of the ability of a compound to reverse multidrug resistance.

The modulation of multidrug resistance demonstrated by the compounds described herein provides a method for treatment of multidrug resistant tumors. The multidrug resistance modulatory properties of the compounds described herein also provide a method for the prevention of the emergence of multidrug resistant tumors during the course of cancer treatment. These same compounds additionally provide a method for reducing the required dosage of an antitumor chemotherapeutic agent.

All of the methods of this invention involve (1) the administration of a compound of the present invention, prior to or concurrent to the administration of an antitumor chemotherapeutic agent; or (2) the administration of a combination of one or more of the compounds of the present invention, and an antitumor chemotherapeutic agent.

For the treatment of multidrug resistant tumor cells the compounds of the present invention either separately or in combination with an antitumor chemotherapeutic agent, may be administered orally, parenterally (including subcutaneous injections, intravenous, intramuscular, intrasternal injection or infusion techniques) or rectally, in dosage unit formulations containing conventional non-toxic, pharmaceutically-acceptable carriers, adjuvants and vehicles.

In particular, the the compounds of the present invention, may be administered either separately or in combination with an appropriate antitumor chemotherapeutic agents such as vinblastine, vincristine, dactinomycin, daunorubicin, doxorubicin, etoposide or mithramycin.

Because of the compounds of the present invention exhibit appreciable oral activity, the preferred mode of administration may be that in which a compound of this invention is administered orally. However, parenteral administration may be preferable in certain circumstances and the precise mode of administration is left to the discretion of the practitioner.

The compounds of the present invention are most easily administered in the form of a pharmaceutically acceptable non-toxic acid addition salt formed from the compound and an organic or inorganic acid recognized in the art as providing a pharmaceutically acceptable non-toxic acid addition salt of these compounds which are formed, e.g., from inorganic or organic acids. Examples of such acid addition salts include acetate, aspartate, benzoate, benzenesulfonate, bisulfate, butyrate, citrate, dihydrogen phosphate, dodecylsulfate, ethanesulfonate, fumarate, hydrochloride, hydrobromide hydroiodide, lactate, maleate, methanesulfonate, 2-naphthalenesulfonate, nicotinate, oxalate, propionate, succinate, sulfate, tartrate, thiocyanate, tosylate, maleate, fumarate, or the like. A more prefered embodiment of the invention is that in which a compound is present as the hydrochloride salt.

The novel compounds of the present invention possess activity in increasing the sensitivity of multidrug resistant mammalian cells to antitumor chemotherapeutic agents in culture and are useful in the treatment of patients afflicted with multidrug resistant tumors.

The pharmaceutical compositions of this invention can be used in the form of a pharmaceutical preparation, for example, in solid, semisolid or liquid form, which contains one or more of the compounds of the present invention, as an active ingredient, in admixture with an organic or inorganic carrier or excipient suitable for enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semisolid, or liquid form, and in addition auxiliary, stabilizing, thickening and coloring agents and perfumes may be used. The active object compound is included in the pharmaceutical composition in an amount sufficient to produce the desired effect upon the process or condition of diseases.

This invention also relates to a method for the reversal of multidrug resistance in patients afflicted with multidrug resistant tumors in need of such therapy a pharmaceutical composition comprising a pharmaceutical carrier and a therapeutically-effective amount of a compound of the present invention or a pharmaceutically acceptable acid addition salt thereof in combination with an anticancer agent.

As implied earlier, the compounds of this invention may be administered by a variety of established methods, including intravenously, intramuscularly, subcutaneously, rectally and orally. Since the compounds of the invention exhibit appreciable oral activity, the preferred mode of administration is that in which a compound of this invention is administrated orally. However, intravenous administration may be preferable in certain circumstances and the precise mode of administration is left to the discretion of the practitioner.

The pharmaceutical compositions containing the active ingredient may be in a form suitable for oral use, for example, as tablets, troches, lozenges, aqueous or oil suspensions, dispersible powders or granules, emulsions, hard or soft capsules, or syrups or elixers. Compositions intended for oral use may be prepared according to any method known to the art for the manufacture of pharmaceutical compositions and such compositions may contain one or more agents selected from the group consisting of a sweetening agents such as sucrose, lactose, or saccharin, flavoring agents such as peppermint, oil of wintergreen or cherry, coloring agents and preserving agents in order to provide pharmaceutically elegant and palatable preparation. Tablets containing the active ingredient in admixture with non-toxic pharmaceutically acceptable excipients may also be manufactured by known methods. The excipients used may be, for example, (1) inert diluents such as calcium carbonate, lactose, calcium phosphate or sodium phosphate; (2) granulating and disintegrating agents such as corn starch, potato starch or alginic acid; (3) binding agents such as gum tragacanth, corn starch, gelatin or acacia, and (4) lubricating agents such as magnesium stearate, stearic acid or talc. The tablets may be uncoated or they may be coated by know techniques to delay disintegration and absorption in the gastrointestinal tract and thereby provide a sustained action over a longer period. For period, a time delay material such as glyceryl monostearate or glyceryl distearate may be employed. They may also be coated by the techniques described in the U.S. Pat. Nos. 4,256,108; 4,160,452; and 4,265,874 to form osmotic therapeutic tablets for controlled release.

In some cases, formulations for oral use may be in the form of hard gelatin capsules wherein the active ingredient is mixed with an inert solid diluent, for example, calcium carbonate, calcium phosphate or kaolin. They may also be in the form of soft gelatin capsules wherein the active ingredient is mixed with water or an oil medium, for example peanut oil, liquid paraffin, or olive oil.

Aqueous suspensions normally contain the active materials in admixture with excipients suitable for the manufacture of aqueous suspensions. Such excipients may be
 (1) suspending agents such as sodium carboxymethylcellulose, methylcellulose, hdyroxypropylmethylcellulose, sodium alginate, polyvinylpyrrolidone, gum tragacanth and gum acacia;
 (2) dispersing or wetting agents which may be
  (a) a naturally-occurring phosphatide such as lecithin, (b) a condensation product of an alkylene oxide with a fatty acid, for example, polyoxyethylene stearate, (c) a condensation product of an ethylene oxide with a long chain aliphatic alcohol, for example, heptadecaethyleneoxycetaonl, (d) a condensation product of ethylene oxide with a partial ester derived from a fatty acid and a hexitol such as polyoxyethylene sorbital monoleate, or (e) a condensation product of ethylene oxide with a partial ester derived from a fatty acid and a hexitol anhydride, for example polyoxyethylene sorbitan monooleate.

The aqueous suspensions may also contain one or more preservatives, for example, ethyl or n-propyl p-hydroxybenzoate; one for more coloring agents; one or more flavoring agents; and one or more sweetening agents such as sucrose or saccharin.

Oily suspension may be formulated by suspending the active ingredient in a vegetable oil, for example, arachis oil, olive oil, sesame oil or coconut oil, or in a mineral oil such as liquid paraffin. The oil suspensions may contain a thickening agent, for example beeswax, hard paraffin or cetyl alcohol. Sweetening agents and flavoring agents may be added to provide a palatable oral preparation. These compositions may be prepared by the addition of an antioxidant such as ascorbic acid.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example, those sweetening, flavoring and coloring agents described above may also be present.

The pharmaceutical compositions of the invention may also be in the form of oil-in-water emulsions. The oily phase may be a vegetable oil such as olive oil or arachis oils, or a mineral oil such as liquid paraffin or a mixture thereof. Suitable emulsifying agents may be (1) naturally, occurring gums such as gum acacia and gum tragacanth, (2) naturally-occurring phosphatides such as soy bean and lecithin, (3) esters or partial esters derived from fatty acids and hexitol anhydrides, for example, sorbitan monooleate, (4) condensation products of said partial esters with ethylene oxide, for example, polyoxyethylene sorbitan monooleate. The emulsions may also contain sweetening and flavoring agents.

Syrups and elixirs may be formulated with sweetening agents, for example, glycerol, propylene glycol, sorbitol or sucrose. Such formulations may also contain a demulcent, a preservative such as methyl and propyl parabans, flavoring such as cherry or orange flavor and coloring agents.

The pharmaceutical compositions may be in the form of a sterile injectable aqueous or oleagenous suspension. This suspension may be formulated according to known methods using those suitable dispersing or wetting agents and suspending agents which have been mentioned above. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose may bland fixed oil may be employed including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate or the like. Buffers, preservatives, antioxidants and the like can be incorporated as required.

A compound of the present invention may also be administered in the form of suppositories for rectal administration of the drug. These compositions may be prepared by mixing the drug with a suitable non-irritating excipient, such as cocoa butter, synthetic glyceride esters or polyethylene glycols, which are solid at ordinary temperatures, but liquify and/or dissolve in the rectal cavity to release the drug.

Since an individual patient may present a wide variation in severity of symptoms and each drug has its unique therapeutic characteristics, it is up to the practitioner to determine the patient's response to treatment and vary the dosages accordingly.

For the reversal of multidrug resistance the daily oral dose, in general, lies within the range of from about to about 0.5 $\mu$g to about 10 mg per kg body weight and, preferably, within the the range of from 50 $\mu$g to 1 mg per kg body weight and can be administered in up to four times daily. The daily IV dose for the reversal of multidrug resistance lies within the range of from about 1 $\mu$g to about 10 mg per kg body weight and, preferably, within the range of from 10 $\mu$g to 500 $\mu$g per kg body weight.

For the treatment of multidrug resistant tumors the compounds of the present invention may be utilized to sensitize multidrug resistant tumor cells to antitumor chemotherapeutic agents and also to reduce the effective dosage of an antitumor chemotherapeutic agent during the course of treatment. For these purposes, the compounds of this invention maybe utilized with one or more chemotherapeutic agents which are useful in treating cancer selected from the group consisting of: vinblastine, vincristine, dactinomycin, daunorubicin, doxorubicin, mithramycin, bleomycin, actinomycin D, etoposide, teniposide, and mitomycin-C. The compounds of the present invention may be administered in combination with, in conjuction with, prior to or concurrent to the administration of antitumor chemotherapeutic agents.

For example, the compounds of the present invention can be given in combinations with such compounds (or combinations of such compounds) or salt or other derivative forms thereof as: vinblastine, vincristine, dactinomycin, daunorubicin, doxorubicin, actinomycin D, etoposide and mithramycin.

For the treatment of multidrug resistance it is preferred that the compounds of the present invention be administered in combination with or concurrent to the administration of an antitumor chemotherapeutic agent.

The weight ratio of a compound of the present invention to the antitumor chemotherapeutic agent or compound may be varied and will depend upon the the effective dose or each ingredient.

Generally, an effective dose of each will be used. Thus, for example, when a compound of the present invention is combined with vinblastine, vincristine, dactinomycin, daunorubicin, doxorubicin or mithramycin, the weight ratio of the compound of the present invention to vinblastine, vincristine, dactinomycin, daunorubicin, doxorubicin or mithramycin, ranges from about 1000:1 to about 1:1000, preferably about 100:1 to 1:100. Combinations of a compound of the present invention and an anticancer agent or compound will generally also be within the aforementioned range, but in each case, an effective dose of each active ingredient should be used.

The following examples are included to illustrate the preparation of the compounds of the present invention and their use in the preparation of representative dosage forms and the preparation of sterile solutions for use in the treatment of patients with multidrug resistant tumors. It is intended that the specification and examples be considered as exemplary only, with the true scope and spirit of the invention being included by the claims of the invention.

EXAMPLE 1

4-Amino-5-chloro-2-methoxy-N-((5-(1-methyl-4-piperidinylidene)-5H-dibenzo[a,d]cyclohepten-3-yl)methyl)benzamide Step A: Preparation of 1-Methyl-4-(3-aminomethyl-5H-dibenzo[a,d]cycloheptene-5-ylidene)piperidine To a suspension of 0.50 g (0.0125 mol) of lithium aluminum hydride in 30 ml of a tetrahydrofuran was added dropwise over 30 minutes a solution of 3.92 g (0.0125 mol) of 1-methyl-4-(3-cyano-5H-dibenzo-[a,d-]cycloheptene-5-ylidene)piperidine (prepared as described in U.S. Pat. No. 3,988,342 (1976), herein incorporated by reference) in 50 ml of tetrahydrofuran. The mixture was stirred at room temperature for 3 hours and then was heated under reflux for one hour. A saturated solution of Rochelles' salt was added dropwise to the cooled, stirred mixture until a clear colorless organic phase was obtained. The inorganic salts remained as a thick paste on the bottom of the flask. The organic phase was decanted and the inorganic residues were extracted twice with hot toluene. The total organic phases were combined and evaporated to dryness. The residue was purified by chromatography on silica gel using chloroform saturated with ammonia gas as an eluant.

The fractions homogeneous by TLC were pooled and evaporated to give 2.94 g (75%) of 1-methyl-4-(3-aminomethyl-5H-dibenzo[a,d]cycloheptene-5-ylidene)-piperidine as an oil. A dihydrochloride salt was prepared and was recrystallized from ethanol-ether, mp 263°–265° C.

Anal. Calcd. for $C_{22}H_{24}N_2 \cdot 2 \; HCl \cdot 0.5 \; H_2O$: C, 66.36; H, 6.84; N, 7.04; Cl, 17.81; Found: C, 66.56; H, 7.17; N, 7.03; Cl, 17.51.

Step B: Preparation of 4-Amino-5-chloro-2-methoxy-N-(5-(1-methyl-4-piperidinylidene)-5H-dibenzo[a,d]cyclohepten-3-yl)methyl)benzamide To a solution of 0.6 g (3.2 mmole) of 4-amino-5-chloro-2-methoxybenzoic acid in 15 ml of methylene chloride cooled to −15° C. was added 0.347 g (3.7 mmol) of ethyl chloroformate. The solution was stirred for 30 minutes and 1.0 g (3.2 mmole) of 1-methyl-4-(3-aminomethyl-5H-dibenzo[a,d]cycloheptene-5-ylidene)-piperidine in 10 ml of methylene chloride was added. The solution was allowed to stir at room temperature for 2 hours. The solution was washed with 1 N sodium hydroxide solution, water, and brine, and then was dried (MgSO$_4$). After filtration, the solvent was removed under reduced pressure to give 4-amino-5-chloro-2-methoxy-N-((5-(1-methyl-4-piperidinylidene)-5H-dibenzo[a,d]cyclohepten-3-yl)methyl)benzamide as an amorphous foam.

Anal. Calcd. for $C_{30}H_{30}ClN_3O_2$: C, 72.06; H, 6.05; N, 8.40; Found: C, 71.67; H, 6.16; N, 8.13.

NMR (CDCl$_3$); δ 2.2 (s, N-$\overline{\text{CH}}$); 2.0–2.5 (m, aliphatic piperidine hydrogens), 3.8 (s, O$\overline{\text{CH}}_3$); 4.4 (s,NH$_2$), 4.6 (d of d CH—N—), 6.9 (s, CH=CH), 7.1–7.4 (m, ArH); 7.9 (t, —$\overline{\text{CH}_2\text{NH}}$—), 8.2 (s, ArH).

EXAMPLE 2

3,4,5-Trimethoxy-N-((5-(1-methyl-4-piperidinylidene)-5H-dibenzo[a,d]cyclohepten-3-yl)methyl)benzamide To a mixture of 0.50 g (1.26 mmol) of the dihydrochloride salt of 1-methyl-4-(3-aminomethyl-5H-dibenzo[a,d]cycloheptene-5-ylidene)piperidine and 0.25 g (1.08 mmol) 3,4,5-trimethoxybenzoyl chloride in 25 ml of toluene was added 1 ml of 10% aqueous sodium hydroxide. The mixture was shaken vigorously for 5 minutes. The toluene was removed by evaporation under reduced pressure and the residual gum was redissolved in chloroform. This chloroform phase was separated, dried over magnesium sulfate, filtered, and the chloroform was removed by evaporation. The crystalline residue was recrystallized from acetonitrile to give 3,4,5-trimethoxy-N-((5-(1-methyl-4-piperidinylidene)-5H-dibenzo[a,d]cyclohepten-3-yl)methylbenzamide, mp 200°–202° C.

Anal. Calcd. for $C_{32}H_{34}N_2O_4$: C, 75.27; H, 6.71; N, 5.49; Found: C, 75.27; H, 6.92; N, 5.77.

EXAMPLE 3

Diethyl 1,4-dihydro-2,6-dimethyl-4-(5-(1-methyl-4-piperidinylidene)-5H-dibenzo[a,d]cyclohepten-3-yl)pyridine dicarboxylate Step A: Preparation of 1-Methyl-4-(3-formyl-5-H-dibenzo[a,d]cycloheptene-5-ylidene)piperidine A mixture of 1.70 g of 1-methyl-4-(3-cyano-5H-dibenzo[a,d]cycloheptene-5-ylidene)piperidine (prepared as described in U.S. Pat. No. 3,988,342 (1976)), 1.70 g of Raney nickel-ammonium alloy, and 25 ml of 75% aqueous formic acid was stirred under reflux for 1.5 hours. The cooled mixture was filtered and the filtrate was made basic by the additional of solid sodium bicarbonate. Extraction of the neutralized mixture with chloroform and evaporation of the solvent gave 1.30 g of 1-methyl-4-(3-formyl-5H-dibenzo[a,d]cycloheptene-5-ylidene)piperidine.

Step B: Preparation of Diethyl 1,4-dihydro-2,6-dimethyl-4-(5-(1-methyl-4-piperidinylidene)-5H-dibenzo[a,d]cyclohepten-3-yl)-pyridine-dicarboxylate A solution of 1.30 g (4.12 mmol) of 1-methyl-4-(3-formyl-5H-dibenzo[a,d]cycloheptene-5-ylidene)piperidine, 1.07 g (8.24 mmol) of ethyl acetoacetate, 0.51 ml of concentrated ammonium hydroxide, and 8 ml of ethanol was stired under reflux for 24 hours. An additional 0.26 g of ethyl acetoacetate and 0.20 ml of concentrated ammonium hydroxide was added, and the solution was refluxed an additional 24 hours.

The solvent was evaporated and the crude product was purified by flash chromatography on silica gel using 10% methanol in chloroform. Evaporation of eluant gave crystalline diethyl 1,4-dihydro-2,6-dimethyl-4-(5-(1-methyl-4-piperidinylidene)-5H-dibenzo[a,d]cyclohepten-3-yl)-pyridine dicarboxylate that was recrystallized from acetonitrile to afford 0.65 g of pure diethyl 1,4-dihydro-2,6-dimethyl-4-(5-(1-methyl-4-piperidinylidene)-5H-dibenzo[a,d]cyclohepten-3-yl)-pyridine-dicarboxylate; mp 204°–206° C.

Anal. Calcd. for $C_{34}H_{38}N_2O_4$: C, 75.81; H, 7.11; N, 5.20; Found: C, 75.78; H, 7.31; N, 5.60.

EXAMPLE 4

| EXAMPLE 4 Dry-Filled Capsules Containing 5 mg of Active Ingredient Per Capsule | Per Capsule |
|---|---|
| (−)-1-Cyclopropylmethyl-4-(3-trifluoromethylthio-5H-dibenzo[a,d]cyclohepten-5-ylidene)-piperidine-hydrochloride | 5 mg |
| Starch | 88 mg |
| Magnesium stearate | 7 mg |

The (−)-1-cyclopropylmethyl-4-(3-trifluoromethylthio-5H-dibenzo[a,d]cyclohepten-5-ylidene)piperidine hydrochloride (5 mg) is reduced to a No. 60 powder and then starch (88 mg) and magnesium stearate (7 mg) are passed through a No. 60 bolting cloth onto the powder and the combined ingredients admixed for 10 minutes and then filled into a hard shell capsule of a suitable size at a fill weight of 100 mg per capsule.

Similar dry-filled capsules can be prepared by replacing the active ingredient of the above example by any of the other compounds of this invention.

EXAMPLE 5

| EXAMPLE 5 Dry Filled Capsules Containing 5 mg Of Active Ingredient In Combination With 5 mg Vinblastine (or similar antitumor chemotherapeutic agent) | Per Capsule |
|---|---|
| (−)-1-Cyclopropylmethyl-4-(3-trifluoromethylthio-5H-dibenzo[a,d]cyclohepten-5-ylidene)-piperidine hydrochloride | 5 mg |
| Vinblastine | 5 mg |
| Lactose, U.S.P. | 580 mg |
| Magnesium stearate | 10 mg |

A mixture of vinblastine (5 mg) and (−)-1-cyclopropylmethyl-4-(3-trifluoromethylthio-5H-dibenzo[a,d]cyclohepten-5-ylidene)piperidine hydrochloride (5 mg) is reduced to a No. 60 powder and then lactose (580 mg) and magnesium stearate (10 mg) are passed through a No. 60 bolting cloth onto the powder and the combined ingredients admixed for 10 minutes and then filled into a No. 1 dry gelatin capsule.

Similar dry-filled capsules can be prepared by replacing the active ingredient of the above example by any of the other compounds of this invention or by replacing vinblastine with any other antitumor chemotherapeutic agent.

EXAMPLE 6

| EXAMPLE 6 Tablets Containing 5 mg Of Active Ingredient | Per Tablet |
|---|---|
| (−)-1-Cyclopropylmethyl-4-(3-trifluoromethylthio-5H-dibenzo[a,d]cyclohepten-5-ylidene)-piperidine hydrochloride | 5 mg |
| Corn Starch, U.S.P. | 6 mg |
| Magnesium stearate | 5 mg |
| Dicalcium Phosphate | 252 mg |
| Lactose, U.S.P. | 250 mg |

The active ingredient is blended with the dicalcium phosphate, lactose and about half of the cornstarch. The mixture is then granulated with 15% cornstarch paste (6 mg) and rough-screened. It is dried at 45° C. and screened again through No. 16 screens. The balance of the cornstarch and magnesium stearate is added and the mixture is compressed into tablets, approximately 0.5 inch in diameter each weighing 800 mg.

Similar tablets can be prepared by replacing the active ingredient of the above example by any of the other compounds of this invention.

EXAMPLE 7

Parenteral Solution of the Hydrochloride Salt of (−)-1-Cyclopropylmethyl-4-(3-trifluormethylthio-5H-dibenzo[a,d]cyclohepten-5-ylidene)piperidine (−)-1-Cyclopropylmethyl-4-(3-trifluoromethylthio-5H-dibenzo[a,d]cyclohepten-5ylidene)piperidine hydrochloride (1 mg) is dissolved in 1 ml water and sufficient isotonic buffer to make a final volume of 10 ml and the solution is sterilized by filtration. The water from all sources are pyrogen-free.

EXAMPLE 8

Parenteral Solution of the Hydrochloride Salt of 4-Amino-5-chloro-2-methoxy-N-((5(1-methyl-4-piperidinylidene)-5H-dibenzo[a,d]cyclohepten-3-yl)-methyl)benzamide 4-Amino-5-chloro-2-methoxy-N-((5-(1-methyl-4-piperidinylidene)-5H-dibenzo[a,d]cyclohepten-3-yl)-methyl)benzamide (1 mg) is dissolved in 1 ml water and sufficient isotonic buffer to make a final volume of 10 ml and the solution is sterilized by filtration. The water from all sources was pyrogen-free.

EXAMPLE 9

Parenteral Solution of the Hydrochloride Salt of 3,4,5-Trimethoxy-N-((5-(1-methyl-4-piperidinylidene) 5H-dibenzo[a,d]cyclohepten-3-yl)methyl)benzamide 3,4,5-Trimethoxy-N-((5-(1-methyl-4-piperidinylidene)-5-dibenzo[a,d]cyclohepten-3-yl)methyl)benzamide hydrochloride (1 mg) is dissolved in 1 ml water and sufficient isotonic buffer to make a final volume of 10 ml and the solution is sterilized by filtration. The water from all sources was pyrogen-free.

EXAMPLE 10

Drug Accumulation: Measurement of the accumulation of [$^3$H] vinblastine in a KB-3 drug-sensitive cell line and a KB-V-1 drug-resistant cell line was performed at 37° C. in serum-free medium (DMEM). Cell monolayers were grown in 24 well dishes. [³H] vinblastine and different compounds (20 μM) were added to cells incubated for 30 minutes, monolayers were washed later, and drug accumulation per mg protein was assayed. As shown in Table 1 and Table 2 the compounds of the present invention have actively in enhancing the accumulation of vinblastine in drug resistant cells.

TABLE 1

ACCUMULATION ASSAY

| | (pmole/mg protein) | |
|---|---|---|
| | KB-V-1 | KB-3 |
| Control | 0.42 ± 0.07 | 4.43 ± 0.21 |
| (−)-1-cyclopropylmethyl-4-(3-trifluoromethylthio-5H-dibenzo[a,d]cyclohepten-5-ylidene)piperidine, | 0.91 ± 0.04 | 11.65 ± 0.11 |
| 4-amino-5-chloro-2-methoxy-N-((5-(1-methyl-4-piperidinylidene)-5H-dibenzo[a,d]cyclohepten-3-yl)methyl)benzamide, | 3.47 ± 0.26 | 3.47 ± 0.15 |
| 3,4,5-trimethoxy-N-((5-(1-methyl-4-piperdinylidene)-5H-dibenzo[a,d]cyclohepten-3-yl)-methyl)benzamide, | 3.31 ± 0.25 | 8.15 ± 0.44 |
| diethyl 1,4-dihydro-2,6-dimethyl-4-(5-(1-methyl-4-piperidinylidene)-5H-dibenzo[a,d]cyclohepten-3-yl)-pyridinedicarboxylate, | 2.13 ± 0.15 | 3.32 ± 0.09 |
| (+)-1-cyclopropylmethyl-4-(3-iodo-5H-dibenzo[a,d]-cyclohepten-5-ylidene)piperidine, | 2.91 ± 0.25 | 7.35 ± 0.18 |
| Verapamil | 2.21 ± 0.18 | 4.65 ± 0.13 |

TABLE 2

ACCUMULATION ASSAY DRUG PREINCUBATED (60 MIN)

| | (pmole/mg protein) | |
|---|---|---|
| | KB-V-1 | KB-3 |
| Control | 0.33 ± 0.06 | 4.46 ± 0.020 |
| (−)-1-cyclopropylmethyl-4-(3-trifluoromethylthio-5H-dibenzo[a,d]cyclohepten-5-ylidene)piperidine, | 1.85 ± 0.11 | 10.16 ± 0.41 |
| 3,4,5-trimethoxy-N-((5-(1-methyl-4-piperdinylidene)-5H-dibenzo[a,d]cyclohepten-3-yl)-methyl)benzamide, | 3.57 ± 0.16 | 3.67 ± 0.32 |
| Verapamil | 2.36 ± 0.21 | 4.71 ± 0.25 |

While the foregoing specification teaches the principles of the present invention, with examples provided for the purpose of illustration, it will be understood that the practice of the invention encompasses all of the casual variations, adaptations, modifications, deletions, or additions of procedures and protocols described herein, as come within the scope of the following claims and its equivalents.

What is claimed is:

1. The compound which is:

4-amino-5-chloro-2-methoxy-N-((5-(1-methyl-4-piperidinylidene)-5H-dibenzo[a,d]cyclohepten-3-yl)-methyl)benzamide;

3,4,5-trimethoxy-N-((5-(1-methyl-4-piperidinylidene)-5H-dibenzo[a,d]cyclohepten-3-yl)methyl)benzamide; or diethyl 1,4-dihydro-2,6-dimethyl-4-(5-(1-methyl-4-piperidinylidene)-5H-dibenzo-[a,d]cyclohepten-3-yl)-pyridinedicarboxylate or pharmaceutically acceptable acid addition salt thereof.

* * * * *